US00PP37527P2

(12) United States Plant Patent
Hansen

(10) Patent No.: US PP37,527 P2
(45) Date of Patent: Jul. 21, 2026

(54) ***HOSTA* PLANT NAMED 'Brotherly Love'**

(50) Latin Name: ***Hosta* hybrid (Tratt.)**
Varietal Denomination: Brotherly Love

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,962

(22) Filed: Dec. 11, 2025

(51) Int. Cl.
*A01H 5/02* (2018.01)
*A01H 6/12* (2018.01)

(52) U.S. Cl.
USPC ..... Plt./353

(58) Field of Classification Search
USPC ..... Plt./263.1, 353
See application file for complete search history.

(56) References Cited

U.S. PATENT DOCUMENTS

PP26,469 P2 * 3/2016 Petryszyn ..... A01H 5/02 Plt./353
PP34,224 P2 * 5/2022 Hansen ..... A01H 6/12 Plt./353

* cited by examiner

*Primary Examiner* — Karen M Redden

(57) ABSTRACT

A new and distinct *Hosta* plant named 'Brotherly Love' has large-sized rounded mounds. The large cordate to broadly ovate foliage are in basal rosettes, with acute apices, cordate bases, and slightly wavy margins. The leaves are variegated with medium green centers and margins of yellowish-chartreuse that lighten to creamy yellow by mid-season. The large-sized leaves have a glaucous matte top and bottom. The large campanulate flowers open to pale purple from medium lavender buds beginning in early July. Each flower is attractively subtended by a floral of pale purple. 'Brotherly Love' is useful in the landscape, as a container plant, a specimen or en masse.

2 Drawing Sheets

Botanical classification: *Hosta* hybrid (Tratt.).
Variety denomination: 'Brotherly Love'.

STATEMENT REGARDING PRIOR DISCLOSURES UNDER 37 CFR 1.77(B)(6)

*Hosta* 'Brotherly Love' was first introduced by the inventor as a non-enabling description in registration of the name in early 2025 with the International Cultivar Registration Authority for the genus *Hosta*. No plants of *Hosta* 'Brotherly Love' have been sold in this country or anywhere in the world, nor has any enabling disclosure of the new plant been made.

BACKGROUND AND ORIGIN OF THE PLANT

The present invention relates to a new and distinct *Hosta* plant, *Hosta* 'Brotherly Love' hereinafter also referred to as the new plant or by the cultivar name 'Brotherly Love'. *Hosta* 'Brotherly Love' was discovered by the inventor in the summer of 2015, at a wholesale perennial nursery in Zeeland, Michigan, USA as a whole plant mutation found in a tissue culture propagated batch of 'Coast to Coast' U.S. Plant Pat. No. 26,469.

'Brotherly Love' has been asexually propagated by division at the same nursery since 2023, and also by careful shoot tip plant tissue culture with the resultant asexually propagated plants having retained all the same traits as the original plant. *Hosta* 'Brotherly Love' has been stable and reproduced true to type plants in successive generations of asexual reproduction.

There are over 7,000 registered and established *Hosta* cultivars with The American *Hosta* Society, which is the International Cultivar Registration Authority for the genus *Hosta*. Several of these are variegated with dark-green leaf blades with broad yellowish margins. The most similar *Hosta* cultivars known to the applicant are: 'Afterglow' U.S. Plant Pat. No. 26,755, 'Atlantis' U.S. Plant Pat. No. 17,093, 'Climax' (not patented), 'Gigantosaurus' U.S. Plant Pat. No. 35,135, 'Lone Star' U.S. Plant Pat. No. 35,134, 'Terms of Endearment' U.S. Plant Pat. No. 34,806, and 'Twin Cities' U.S. Plant Pat. No. 34,984.

'Afterglow' has foliage that is more bullate with a flatter margin, and the variegated margin is wider. 'Atlantis' has more ovate leaves with more narrowly acute apices and the leaves have a coarse wave and slight undulation. 'Climax' has foliage with a more bullate surface, the variegated margin is more yellowish-chartreuse, and the scapes are more arching. 'Gigantosaurus' has a larger, longer, broader and more ovate, and more arching foliage with a narrower variegated margin. 'Lone Star' has foliage that is more ovate and less rounded, the variegated margins are narrower and remain more yellowish through the growing season, the leaves are flatter and less bullate, and scapes are much taller. 'Terms of Endearment' has longer and broader foliage that is more glaucous and more arching, and the flowers are more pale purple to white. 'Twin Cities' has a stiffer and thicker substance foliage that is broader and longer and more bullate, and variegated margin transitions from chartreuse to more yellow by mid-season.

The parent is slightly smaller in both habit and foliage size, and the foliage is not variegated but comprises a variable combination of chartreuse and yellow.

Other *Hosta* cultivars may have individual traits similar to 'Brotherly Love' but the new plant differs from the above listed cultivars and all other *Hostas* known to the applicant, by the combination of the following traits.

1. Leaves are large-sized, cordate to broadly ovate, with acute apices and cordate bases;
2. Leaves are lightly bullate with a slightly wavy margin, and have lightly impressed adaxial veins;
3. Leaf margins are yellowish-chartreuse and lighten to creamy yellow by mid-season, and the center is medium green;
4. Large campanulate flowers are medium lavender in bud and open to pale purple closely arranged on scapes just above the foliage beginning in early July;
5. Floral bracts of pale lavender subtend each flower;
6. The plant has large-sized rounded mound habit.

BRIEF DESCRIPTION OF THE DRAWING

The photograph of the new plant demonstrates the overall appearance of the new plant, including the unique traits. The colors are as accurate as reasonably possible with color reproductions. Ambient light spectrum, temperature, source and direction may cause the appearance of minor variation in color.

The drawings show five-year-old plants of 'Brotherly Love' plant in a trial garden at a nursery in Zeeland, MI with supplement fertilizer and water as needed.

DETAILED BOTANICAL DESCRIPTION

Figure 1:
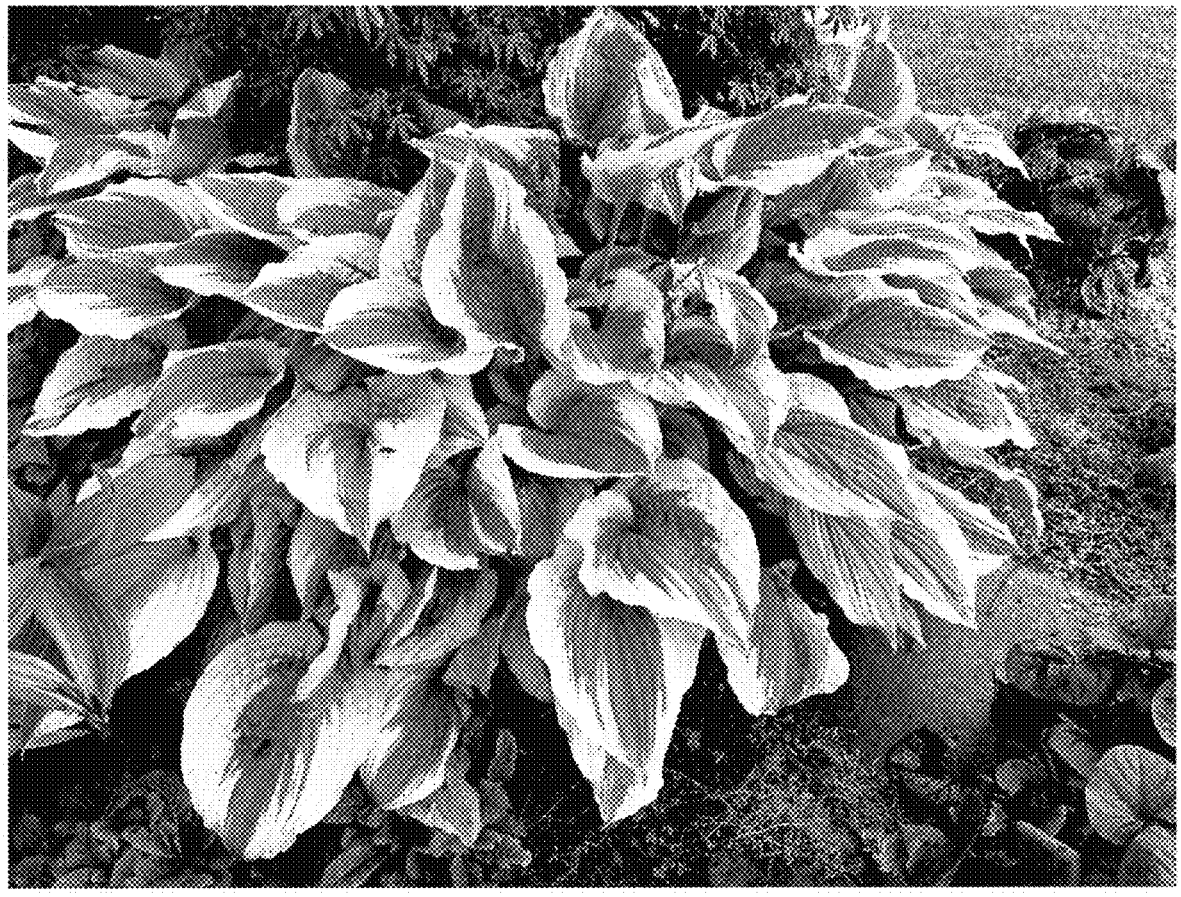
FIG. 1 shows the landscape foliage habit of a new plant.
Figure 2:
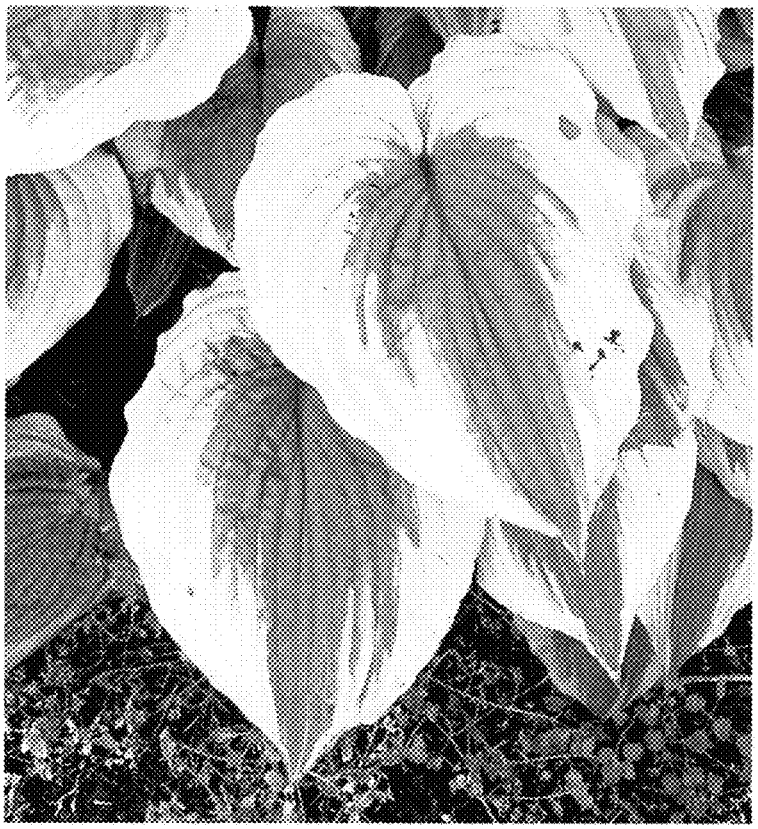
FIG. 2 shows a close-up of leaves.
Figure 3:
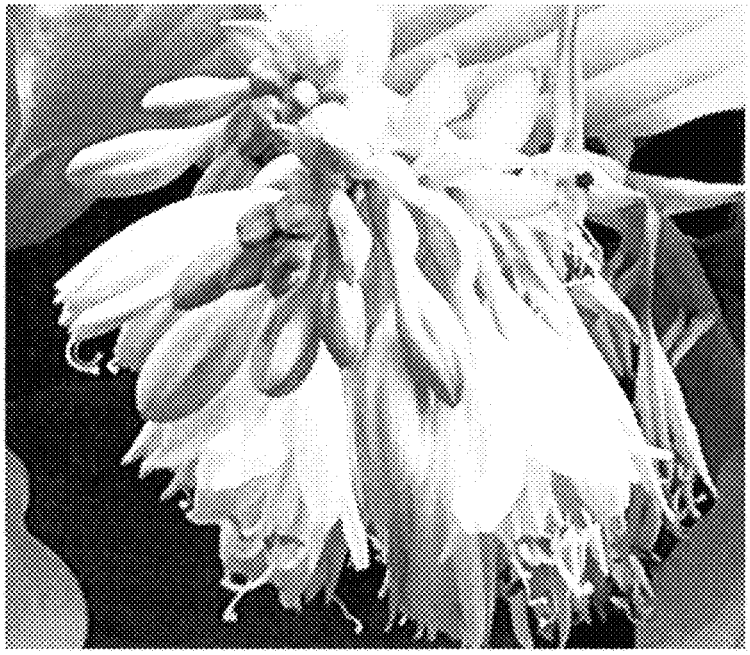
FIG. 3 shows a close-up of the scape with flowers, buds, and foliar bracts.

The following descriptions and color references are based on the 2015 edition of The Royal Horticultural Society Colour Chart except where common dictionary terms are used. The new plant, *Hosta* 'Brotherly Love', has not been observed in all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a three-year-old plant in a shaded trial garden in Zeeland, Michigan with supplemental water and fertilizer as needed.

Botanical classification: *Hosta* x hybrid;

Parentage: The parent 'Coast to Coast';

Propagation: Garden division and sterile shoot tip tissue culture;

Time to initiate roots from tissue culture: About three weeks;

Growth rate: Moderately vigorous;

Crop time: About three months to four months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with basal rosette of leaves emerging from rhizomes producing a low medium-sized mound of outwardly extending petioles and leaves and arching scapes flowering above foliage;

Plant size: Foliage height to about 89 cm above soil line to the top of the leaves, to about 79 cm tall to the top of the flowers and to about 160 cm wide at the widest point just above the soil line;

Foliage description: Broadly ovate; narrowly acute apex, cordate base, with nearly touching lobes in maturity; margin entire, and slightly sinuate; moderately bullate between the veins; glabrous both surfaces; matte adaxial and glaucous abaxial; flexible; variegated;

Leaf blade size: To about 29.5 cm long and about 22.9 cm wide about one-third way from the base; variegated margin varies from 3.8 cm up to 7.6 cm wide with maturity;

Leaf blade color: Early season and expanding adaxial margin between RHS 144B and RHS 146D, center between RHS 138A and RHS 144A, intermediate colors comprising nearest RHS 144A and nearest RHS 144B; abaxial early season and expanding margin between RHS 147C and RHS 145A, center between RHS 194A and RHS 139C; mid-season and late summer adaxial margin between RHS 151A and RHS 146D, center between RHS 138B and RHS 146B, with intermediate zone comprising colors of between RHS 144A and RHS 144B, between RHS 145A and RHS 146B, and nearest RHS 144B; abaxial mid-season and late summer margin between RHS 146D and RHS N147C, center between RHS 191B and RHS N138C, with intermediate zone comprising between RHS 144B and RHS 191C;

Veins: 12 to 13 pairs with midrib; impressed adaxial and costate and smooth abaxial;

Vein color: Young adaxial margin region nearest RHS N138B and center nearest RHS 146D, young abaxial margin region nearest RHS N138B and center nearest RHS 148C; mature adaxial margin nearest RHS 144C, and center nearest RHS 148B; mature abaxial margin between RHS 191B and RHS 160C, and center nearest RHS 148C;

Petiole: Glabrous and glaucous both adaxial and abaxial; moderately concavo-convex; stiff; to 46 cm long and 20 mm wide at base and about 7 mm deep; with a lightly variegated margin about 2 mm wide;

Petiole color: Adaxial and abaxial margin nearest RHS 144A, adaxial midrib and surrounding center between RHS 146B and RHS 147B with about three longitudinal streaks in distal one-third just inside margin nearest RHS 138A; abaxial midrib nearest RHS nearest RHS 145D in the distal one-half, proximal one-half midrib and entire length between midrib and margin nearest RHS 144D except just inside the margin on the distal one-half nearest RHS 137C;

Flower description:

Buds one to two days prior to opening: Clavate with acute apex and narrow tube and rounded base; about 40 mm long and 11 mm in diameter at the widest portion in the bulb, tube to about 13 mm long and to about 3 mm diameter at base, quickly tapering from bulb;

Bud color: Distal tube and proximal half of bulb between RHS NN155D and RHS 85D with distal half of bulb nearest RHS 85D with tepal margins nearest RHS 85C; and proximal half of tube nearest RHS 85D;

Flowers: Perfect; incomplete; broadly campanulate; attitude outwardly; to 58 mm long to exserted pistil; corolla to 46 mm long and 37 mm wide at apex, fused in basal 26 mm, free in the distal 20 mm, decreasing in size distally; corolla tube portion about 18 mm long and quickly tapering to 3 mm diameter in middle; with rounded base; flowers tightly arranged on scape;

Flowering lasting: Persists for a normal period, usually about one day on plant;

Flowering period: Scapes remain effective with flowers beginning early-July for about three weeks; with about 32 flowers per scape; mostly secund;

Fragrance: No detectable fragrance;

Tepal: Two sets of three; lanceolate; entire margins; outer set with acute apex, inner set with rounded apex; fused in basal 26 mm; glabrous adaxial and abaxial; outer set to about 10 mm wide and 49 mm long; inner set to about 11 mm wide and 49 mm long;

Tepal color: Outer and inner sets adaxial blades nearest RHS 85D in the longitudinal center and between RHS NN155D and RHS 85D along the margins, and the corolla tube nearest RHS NN155D; abaxial inner set longitudinal center nearest RHS 85D and along margin and corolla tube nearest RHS NN155D with a faint blush of nearest RHS 85D; abaxial outer set nearest RHS NN155D with a faint blush of nearest RHS 85D;

Gynoecium: Single; to about 60 mm long; superior;

*Style*.—Cylindrical; glabrous; to about 51 mm long and 1 mm diameter; straight with distal 10 mm arcuate upwards 90°; color nearest RHS 155C.

*Stigma*.—Globose; puberulent; about 1 mm long and 1.5 mm diameter; color nearest RHS NN155A.

*Ovary*.—Ellipsoidal; superior; apex rounded; base rounded to truncate; sides deeply furrowed; lustrous; about 8 mm long and 2.5 mm diameter; color nearest RHS 143C.

Androecium: Six;

*Filaments*.—Six; cylindrical; approximately 52 mm long and 0.5 mm in diameter; curved or bent upwardly about 90° in the distal 10 mm; color nearest RHS 155C.

*Anthers*.—Oblong with rounded ends; basifixed, longitudinally dehiscent; about 6 mm long and 2.5 mm wide when fully developed in unopened flower; color adaxial with alternating longitudinal lines of nearest RHS 199C and RHS 163C, abaxial nearest RHS 18C.

*Pollen*.—Abundant; spherical; less than 0.1 mm long; color nearest RHS 17A.

Peduncle: Cylindrical; usually one per mature division; about 4 per plant; glabrous; moderately glaucous; aspect arching slightly outwardly; to about 78 cm long, and about 8 mm in diameter at base, average about 70 cm long and 6 mm diameter at base;

Peduncle color: Proximally between RHS 143A and RHS 144A, distally nearest RHS 85D;

Inflorescence: Flowering portion about 28 cm long and 9 cm wide; with bracts subtending each flower;

Pedicel: Cylindrical; glabrous; slightly lustrous; to about 8 mm long and 2 mm diameter; slightly arcuate sideways; attitude outwardly;

Pedicel color: Nearest RHS 76C;

Bracts: Typically one subtending each flower; lanceolate; narrowly acute apex and truncate base and clasping; entire margin; glabrous and slightly glaucous abaxial and adaxial; to about 16 mm long 6 mm wide, decreasing distally; margin about 1 mm wide;

Bract color: At flowering adaxial and abaxial margin nearest RHS 138B, adaxial and abaxial center between RHS N155B and RHS 76D;

Fruit and seeds: Not yet observed;

Disease resistance: Resistance and susceptibility to pests (including: *Odocoileus virginianus* and *Oryctotagus cuniculus*) and diseases common to *Hostas* is equal that typical of other cultivars.

Growth: The plant grows best and shows best coloration with plenty of moisture, adequate drainage and light shade, but is able to tolerate some drought when mature.

Hardiness: At least from USDA zone 3 through 8, and other disease resistance is typical of that of other *Hostas*.

It is claimed:

1. A new and distinct *Hosta* plant named 'Brotherly Love' as herein described and illustrated.

* * * * *